United States Patent [19]
Griffiths et al.

[11] Patent Number: 6,077,499
[45] Date of Patent: Jun. 20, 2000

[54] TARGETED COMBINATION IMMUNOTHERAPY OF CANCER

[75] Inventors: Gary L. Griffiths, Morristown; Hans J. Hansen, Mystic Island, both of N.J.

[73] Assignee: Immunomedics, Inc., Morris Plains, N.J.

[21] Appl. No.: 09/184,950

[22] Filed: Nov. 3, 1998

Related U.S. Application Data

[60] Provisional application No. 60/017,011, May 3, 1996.

[51] Int. Cl.$^7$ ............................. A61K 51/00; A61M 36/14
[52] U.S. Cl. ......................... 424/1.49; 424/1.11; 424/1.65
[58] Field of Search ................................... 424/1.11, 1.65, 424/1.69, 9.1, 1.37, 1.53, 1.49, 1.41, 1.45, 9.3, 9.4, 9.5, 9.6, 9.7, 9.8, 78.08; 534/7, 10–16; 206/223, 569, 570; 514/2, 12, 387

[56] References Cited

U.S. PATENT DOCUMENTS

| | | | |
|---|---|---|---|
| 4,624,846 | 11/1986 | Goldenberg . | |
| 4,818,684 | 4/1989 | Edelman et al. | 435/7 |
| 5,283,342 | 2/1994 | Gustavson et al. | 548/304.1 |
| 5,420,105 | 5/1995 | Gustavson et al. | 514/2 |
| 5,474,772 | 12/1995 | Maddock | 424/140.1 |
| 5,482,698 | 1/1996 | Griffiths | 424/1.41 |
| 5,525,338 | 6/1996 | Goldenberg . | |
| 5,621,002 | 4/1997 | Bosslet et al. | 514/451 |
| 5,632,990 | 5/1997 | Bagshawe et al. | 424/178.1 |
| 5,683,694 | 11/1997 | Bagshawe et al. | 424/178.1 |
| 5,846,741 | 12/1998 | Griffiths et al. | 435/7.5 |

FOREIGN PATENT DOCUMENTS

97/41898  11/1997  WIPO .

OTHER PUBLICATIONS

Senter et al, Cancer Research, 56, 1471–1474, "The Role of Rat Serum Carboxylesterase in the Activation of Paclitaxel and Camplothecin Prodrugs", Apr. 1996.

Meyer et al, Bioconjugate Chem., 6, 440–446, "Site Specific Prodrug Activation by Antibody–B–Lactamase Conjugates: Preclinical Investigation of the Efficacy & Toxicity of Doxorubicin Delivered by Antibody Directed Catalysts", 1995.

Vitols et al, Cancer Research, 55, 478–481, "Methotrexate–L–phenylalanine: Optimization of Methotrexate prodrug for activation by carboxypeptidas A–Monoclonal Antibody Conjugate", Feb. 1995.

Rodrigues et al, Cancer Research, 55, 63–70, "Development of a Humanized Disulfide Stabilize Anti–p185–Herz FV–B–Lactamase Fusion Protein for activation of a cephalosporin doxorubicin prodrug", Jan. 1995.

Sahin et al, Cancer Research, 50, 6944–6948, "Specific Activation of the prodrug mitomyain phosphate by a bispecific AntiCD30/Anti Alkaline phosphatase monoclonal antibody", Nov. 1990.

Goodman et al, *The Pharmacological Basis of Therapeutics*, $6^{th}$ Edition, pp. 1252–1300, Macmillan Publishing Co; New York, 1980.

O'Donoghue et al., J. Nucl. Med., 36:1902–1909 (Oct. 1995).

*Primary Examiner*—Jose' G. Dees
*Assistant Examiner*—Dameron Jones
*Attorney, Agent, or Firm*—Foley & Lardner

[57] ABSTRACT

The invention provides compositions, methods and kits for effecting therapy of a tumor in a patient. The compositions comprise (A) a first conjugate comprising a targeting moiety, a first member of a binding pair, and a first therapeutic agent, wherein the targeting moiety selectively binds to a marker substance produced by or associated with the tumor; (B) optionally, a clearing composition; and (C) a second conjugate comprising a complementary member of the binding pair and a second therapeutic agent, wherein the second therapeutic agent is the same as or different from the first therapeutic agent. The methods comprise sequentially administering (A), (B), and (C) to a patient. The kits comprise (A), (B), and (C) in separate containers.

37 Claims, 2 Drawing Sheets

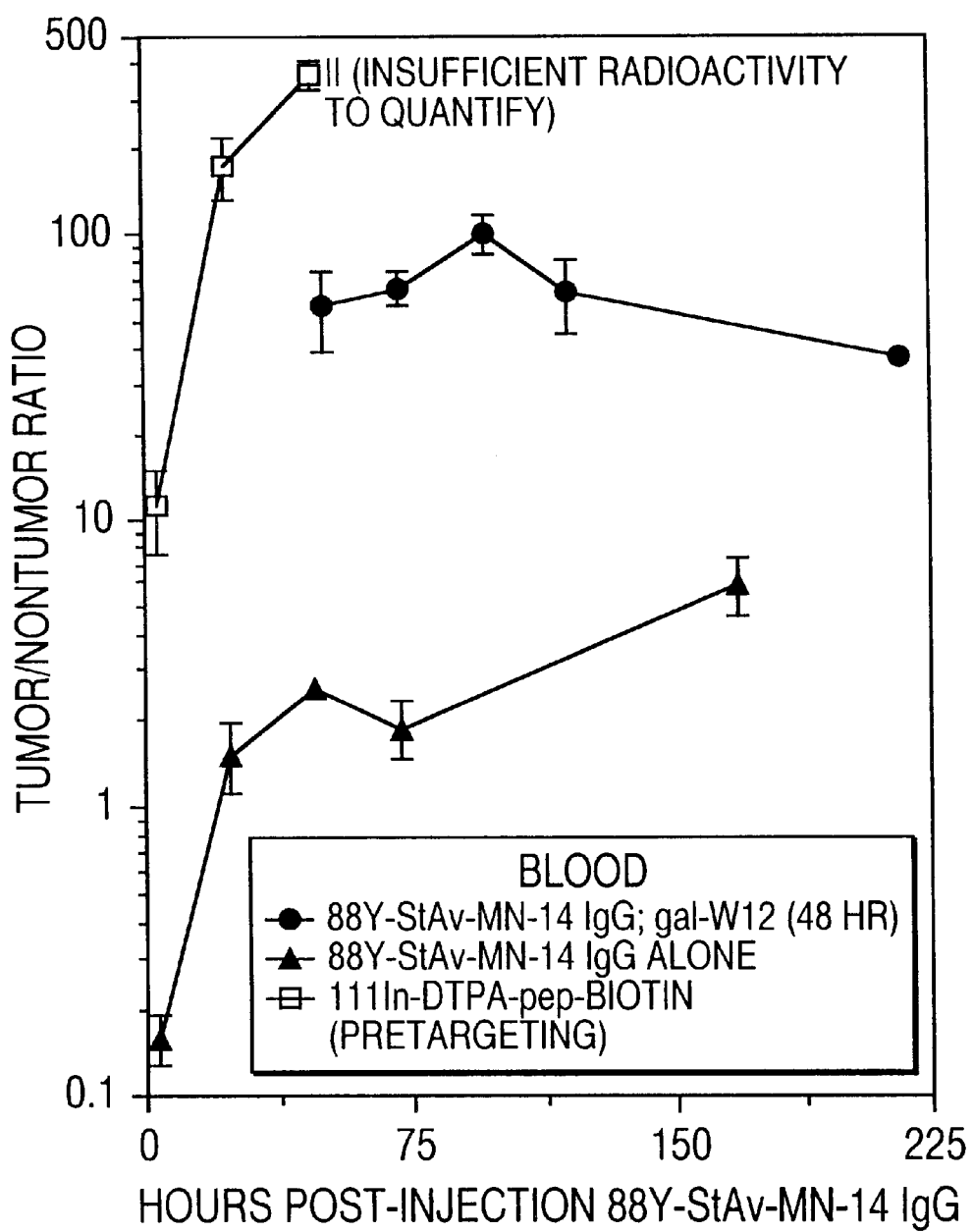

TARGETED COMBINATION IMMUNOTHERAPY OF CANCER

RELATED APPLICATIONS

This application is based on provisional application 60/017,011, filed May 3, 1996, and is the U.S. national stage of PCT/US97/07395, filed May 2, 1997.

BACKGROUND OF THE INVENTION

1. Field of the Invention

The present invention is directed to methods for treating cancer wherein more than one therapeutic agent is used, with each of the therapeutic agents having different tumor-killing capabilities, and wherein the therapeutic agents are delivered to the tumor sites using combined targeting and pre-targeting methods. The methods of the present invention achieve good tumor to non-tumor ratios of the therapeutic agents, and are effective for cancer therapy.

2. Description of Related Art

Target-directed therapy, such as antibody-directed therapy, offers advantages over non-targeted therapy such as systemic therapy via oral or i.v. administration of drugs or whole body therapy such as external radiation therapy (XRT). An advantage of antibody-directed therapy, and of therapy using monoclonal antibodies (MAbs) in particular, is the ability to deliver increased doses of a therapeutic agent to a tumor, with greater sparing of normal tissue from the effects of the therapeutic agent. This directed therapy might include the use of naked MAbs or MAbs conjugated to drugs, bacterial or other toxins, radionuclides, or neutron-capturing agents, such as boron addends.

However, antibody-directed therapies have drawbacks, which include: (1) the inability to target all cancer cells within a tumor due to tumor antigen heterogeneity especially when using non-isotopic therapeutics ; (2) low absolute accretion of antibody in the tumor; and (3) the use of therapeutic conjugates which cause unacceptable normal organ toxicity. The prior art treatment methods have not provided complete solutions to each of these problems.

Methods of increasing the amount of isotope which can be specifically directed to a tumor while at the same time minimizing the amount of time an isotope remains in circulation so that host toxicity is reduced are described in U.S. Pat. Nos. 5,482,698 and 5,525,338, the contents of which are incorporated by reference herein in their entirety. For example, host toxicity may be minimized by using pre-targeting techniques that decouple the isotope delivery step from the antibody localization step. In addition, these patents disclose methods for amplifying the amounts of therapeutic agents which may be delivered to tumor sites. These methods also are useful in accordance with the present invention.

U.S. Pat. No. 4,624,846, discloses methods for reducing host toxicity by administering a second antibody to clear circulating radiolabeled first antibody. Co-pending U.S. application Ser. No. 08/486,166, filed Jun. 7, 1995, the contents of which are incorporated by reference herein in their entirety, teaches the use of an antibody that is anti-idiotypic to the first administered (radiolabeled) primary targeting species as a clearing agent in pre-targeting methods. These methods also may be used in accordance with the present invention, and the contents of the aforementioned patents are incorporated herein by reference in their entirety.

Although these patents and patent applications disclose methods which address several of the problems associated with target-directed therapies, none of them address the problem caused by tumor antigen heterogeneity. Additionally, there is a continuing need to utilize the specificity of a targeting moiety to simultaneously deliver tumor-killing amounts of therapeutic agents to tumors yet sparing the toxic effect of these agents on normal tissues. The present invention provides a solution to these problems by disclosing a method that utilizes multiple targeting and pre-targeting administrations to deliver more than one therapeutic agent to the tumor. Preferably the therapeutic agents have different tumor killing properties so that more cells in the tumor can be targeted and killed. Further, the present methods maximize and amplify the mole amounts of therapeutic agents delivered per mole of antibody to address the low absolute target accretion levels of antibody. To solve the problem of low antibody-to-normal tissue ratios, at least one therapeutic agent is delivered in a later treatment step.

SUMMARY OF THE INVENTION

The present invention provides a tumor therapy method including administering a first conjugate, which contains a tumor targeting moiety, a therapeutic agent, and a first member of a binding pair; then optionally administering a clearing agent to clear non-tumor targeted first conjugates; and then administering a second conjugate, which contains the complementary binding member of the binding pair and a second therapeutic agent.

The method of the present invention delivers more than one therapeutic agent to a tumor site using both targeting and pre-targeting methods to achieve effective and efficient delivery of the agents to the tumor sites.

The present invention provides a therapy method that addresses the problem of tumor heterogeneity by delivering at least two different therapeutic agents having different tumor-killing properties to the tumor sites.

The present invention further provides a therapy method that minimizes patient toxicity caused by the therapeutic agents by using pre-targeting and targeting methods of delivery.

The present invention additionally provides a therapy method with reduced toxic effects on normal tissue by utilizing clearing agents in combination with the targeting and pre-targeting methods of delivering more than one therapeutic agent to efficiently clear non-localized targeting moieties from circulation.

BRIEF DESCRIPTION OF THE DRAWINGS

FIG. 2 shows the tumor-to-blood ratios for Y-88-DTPA-MN14 (anti-CEA)-streptavidin conjugate with and without clearing anti-idiotypic antibody to MN14, WI2; and 111-In-DTPA-pep-Biotin at continuing time points.

DETAILED DESCRIPTION

Figure 1:
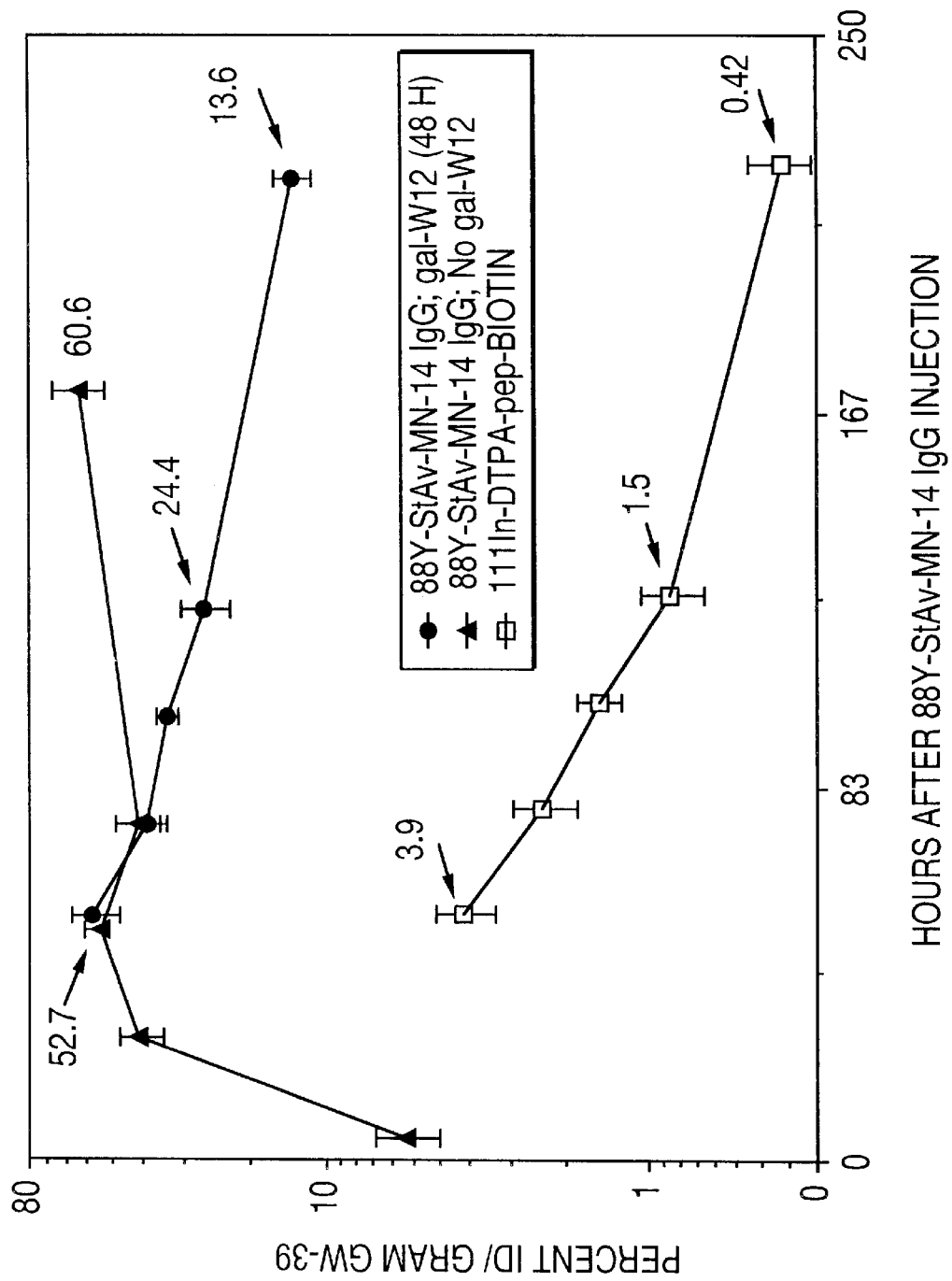
FIG. 1 shows the percentage ID/g of Y-88-DTPA-MN14 (anti-CEA)-streptavidin conjugate with and without clearing anti-idiotypic antibody to MN14, WI2; and 111-In-DTPA-pep-Biotin in tumors at continuing time points.

The present method of therapy specifically includes the following steps:

(A) administering to the patient a first conjugate comprising a targeting moiety, a first member of a binding pair, and a first therapeutic agent, where the targeting moiety selectively binds to a marker substance produced by or associated with said tumor, and allowing the first conjugate to localize at the tumor, thereby effecting therapy on the tumor;

(B) optionally, administering to the patient a clearing composition, and allowing the clearing composition to clear non-localized first conjugate from circulation;

(C) administering to the patient a second conjugate comprising a complementary member of the binding pair and a second therapeutic agent, where the second therapeutic agent is the same as or different from the first therapeutic agent, and allowing the second conjugate to localize at the tumor, thereby effecting therapy of the tumor.

The first and second therapeutic agents are selected from the group consisting of radionuclides, drugs, toxins, and boron addends. If both therapeutic agents are radionuclides, then it is preferably that each of the radionuclides emit different levels of radiation. Preferably the first therapeutic agent is selected from the group consisting of I-131, I-125 and At-211, and the second therapeutic agent is selected from the group consisting of P-32, P-33, Sc-47, Cu-64, Cu-67, As-77, Y-90, Ph-105, Pd-109, Ag-111, I-125, Pr-143, Sm-153, Tb-161, Ho-166, Lu-177, Re-186, Re-188, Re-189, Ir-194, Au-199, Pb-212, and Bi-213.

Alternatively the second therapeutic agent is a boron addend, and the method further comprises irradiating the tumor with thermal or epithermal neutrons after localization of the second conjugate at the tumor.

Further, the first and second therapeutic agents are mixtures of at least two radionuclides, drugs, toxins or boron addends.

In another embodiment of the present invention, the first therapeutic agent is a radionuclide and the second therapeutic agent is a drug, a toxin, or a boron addend.

As described above, the first therapeutic agent is selected from the group consisting of I-131, I-125 and At-211. The second therapeutic agent is a drug and is selected from the group consisting of taxol, nitrogen mustards, ethylenimine derivatives, alkyl sulfonates, nitrosoureas, triazenes, folic acid analogs, pyrimidine analogs, purine analogs, vinca alkaloids, antibiotics, enzymes, platinum coordination complexes, substituted urea, methyl hydrazine derivatives, adrenocortical suppressants, hormones, antagonists, camptothecin, and endostatin. The second therapeutic agent can alternatively be a toxin is selected from the group consisting of abrin, alpha toxin, diphtheria toxin, exotoxin, gelonin, pokeweed antiviral protein, ricin, saporin, and onconase.

In a further embodiment of the present invention the first therapeutic agent is a drug or toxin and the second therapeutic agent is a radionuclide or a boron addend. Examples of useful drugs, toxins, and radionuclides are described above.

The targeting moiety is an antibody or an antigen binding antibody fragment, and preferably is a bispecific antibody capable of specifically binding to at least one epitope on the marker substances associated with, produced by or on the surface of the tumor, or on a component of the second conjugate.

The targeting moiety can also be a non-antibody species selecting from the group consisting of proteins, peptides, polypeptides, enzymes, and oligonucleotides.

The binding pair is selected from the group consisting of avidin or streptavidin and biotin, complementary DNA fragments, complementary peptide oligonucleotides, and corresponding enzymes and prodrug substrates. The binding pair preferably is avidin or streptavidin and biotin. More specifically, the method employs a first conjugate is a radiolabeled monoclonal antibody conjugated to streptavidin, where the monoclonal antibody selectively binds to the marker substance, and the second conjugate is a radiolabeled biotinylated chelate. Preferably, the two radionuclides emit different levels of radiation. The clearing agent binds to the first conjugate. The clearing agent is preferably anti-idiotypic to the targeting moiety, and more specifically an anti-idiotypic monoclonal antibody. More preferably the anti-idiotypic monoclonal antibody is substituted with galactose and biotin residues.

This method specifically addresses the problem of disease heterogeneity which normally presents in a clinical setting. The heterogeneity is addressed by targeting both large tumors and small micrometastases within the same therapeutic method. For example, both a high-energy (highly penetrating) beta-emitter and a low or medium energy beta-emitter which exerts its penetrating effect over much shorter distances are administered to target tumor sites. For treating a disease that is more limited, a medium-energy beta-emitter may be penetrating enough to treat the larger tumors. In this embodiment, both a medium-energy beta-emitter and a low-energy beta-emitter or, preferably, a drug or toxin are delivered to tumor sites.

Cancer sites that can be targeted and treated in accordance with the present invention include carcinomas, melanomas, sarcomas, neuroblastomas, leukemias, lymphomas, gliomas and myelomas. The method is particularly well-suited for therapy of limited metastatic disease, for example, for patients who present with multiple-site tumors, up to about 5 cm in diameter.

Tumors of up to about 5 cm in diameter are those is tumors which are at the maximum effective range of the most penetrating radionuclide usable with radioimmunotherapy, the pure beta-particle-emitting yttrium-90 (Y-90) nuclide. The tumor of optimum diameter for use with this nuclide is one of 3.4 cm, and the isotope's effectiveness falls off dramatically above and below this optimum diameter, such that the optimum range for a tumor targeted with Y-90 is between 2.8 and 4.2 cm. O'Donoghue et al., *J. Nucl. Med.*, 36: 1902–1909 (1995). This isotope will be ineffective against small tumor deposits, and an isotope of shorter range will also be needed for dual isotope radiation. O'Donoghue et al., supra.

A tumor of 5 cm diameter weighs approximately 65 g ($\frac{4}{3}\pi r^3$; where 1 cm$^3$=1 g weight), and contains $6.5\times10^9$ cells. An average cell may be 5–20 micron in diameter. For optimum tumor cell eradication, it appears that an isotope of one particular energy will probably fail to deliver effective toxicity to a tumor in this range. Twenty-two isotopes have been reported that could be used in the context of a doubly radiolabeled antibody. O'Donoghue et al., supra. However, for the very smallest tumor deposits, and for single cells, few of the available isotopes may be useful, and a drug or toxin may be more appropriate.

The method of the present invention comprises at least two steps. In the first step, a conjugate comprising a targeting moiety, a member of a binding pair and a first therapeutic agent is administered. After the first conjugate has been administered and allowed to localize, and, preferably, after time for maximum tumor uptake of the conjugate has passed, a second conjugate is administered. This conjugate comprises the complementary member of the binding pair used in the first step and a second therapeutic agent. This conjugate localizes at the tumor sites by way of the binding pair. For example, if a radiolabeled MAb-avidin conjugate is administered in the first step, the second conjugate comprises biotin. The binding affinity between avidin and biotin will result in the second conjugate binding to the avidin already localized at the tumor sites. As a result, the second conjugate also is localized at the tumor sites. Because each avidin moiety can bind up to four biotin moieties, amplification is achieved in this step.

Optionally, a clearing step may be performed between the two steps described above. That is, after the first conjugate has had time to localize at the tumor sites, a clearing agent may be administered to remove circulating conjugate.

Targeting Moieties

The targeting moiety may be, for example, an antibody or an antigen binding antibody fragment. Monoclonal antibodies are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies also are contemplated, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the present invention include $F(ab')_2$, $F(ab)_2$, Fab', Fab, Fv and the like including hybrid fragments. Preferred fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant antibodies and proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is incorporated herein by reference.

Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin. The fragments may also be produced by genetic engineering.

It should be noted that mixtures of antibodies and immunoglobulin classes can be used, as can hybrid antibodies. Multispecific, including bispecific and hybrid, antibodies and antigen binding antibody fragments are useful in the methods of the present invention. Bispecific and hybrid antibodies are capable of specifically binding to at least one epitope on the marker substances, or on a component of the second conjugate. These antibodies preferably are comprised of at least two different substantially monospecific antibodies or antibody fragments, which specifically bind to at least one epitope on the marker substance produced by or associated with the cancer cells and with at least one epitope of a component of the second conjugate. Multispecific antibodies and antibody fragments with dual specificities can be prepared analogously to the anti-tumor marker hybrids disclosed in U.S. Pat. No. 4,361,544, the contents of which are incorporated by reference herein in their entirety. Other techniques for preparing hybrid antibodies are disclosed in, e.g., U.S. Pat. No. 4,474,893 and 4,479,895, and in Milstein et al., *Immunol. Today*, 5: 299 (1984), the contents of which are incorporated by reference herein in their entirety.

Preferred are antibodies having a specific immunoreactivity to a marker substance produced by or associated with the cancer cells of at least 60% and a cross-reactivity to other antigens or non-targeted substances of less than 35%. A monoclonal antibody that specifically targets tumor sites by binding to antigens produced by or associated with the tumors is particularly preferred.

Antibodies against tumor antigens are known. For example, antibodies and antibody fragments which specifically bind markers produced by or associated with tumors have been disclosed, inter alia, in Hansen et al., U.S. Pat. No. 3,927,193, and Goldenberg U.S. Pat. Nos. 4,331,647, 4,348, 376, 4,361,544, 4,468,457, 4,444,744, 4,818,709 and 4,624, 846, the contents of all of which are incorporated herein by reference in their entirety. In particular, antibodies against an antigen, e.g., a gastrointestinal, lung, breast, prostate, ovarian, testicular, brain or lymphatic tumor, a sarcoma or a melanoma, are advantageously used.

The antibodies and antigen binding antibody fragments useful in the methods of the present invention :may conjugated to the member of the binding pair by a variety of methods known in the art to include chemical conjugation and recombinant methods for making fusion proteins. Many of these methods are disclosed in the above-referenced U.S. patents and patent applications. See also Childs et al., *J. Nuc. Med.*, 26: 293 (1985), the contents of which are incorporated by reference herein in their entirety.

An antibody preferred for use in the present invention is MN-14, a second generation CEA-antibody that has ten times more affinity for CEA than the first generation version, NP-4. Hansen et al., *Cancer*, 71: 3478–85 (1993). MN-14 internalizes slowly, making it suitable for a pre-targeting approach.

Other targeting moieties useful in the present invention include, for example, proteins, peptides, polypeptides, glycoproteins, lipoproteins, phospholipids, oligonucleotides, steroids, alkaloids or the like, e.g., hormones, lymphokines, growth factors, albumin, cytokines, enzymes, immune modulators, receptor proteins, antisense oligonucleotides, antibodies and antibody fragments, which preferentially bind marker substances that are produced by or associated with the target site.

Binding Pair

A common binding pair used in pre-targeting methods is avidin or streptavidin and biotin. Avidin, found in egg whites, has a very high binding affinity for biotin, which is a B-complex vitamin. Wilcheck et al., *Anal. Biochem.*, 171: 1 (1988). Streptavidin, derived from *Streptomyces avidinii*, is similar to avidin, but has lower non-specific tissue binding, and therefore often is used in place of avidin. Both avidin and streptavidin have a tetravalency for biotin, thus permitting amplification when the former bind to biotin. Modified forms of avidin, such as deglycosylated avidin, charge-neutralized avidin, or deglycosylated and charge-neutralized avidin also are useful in the invention.

As used herein, "biotin" includes biotin, commercial biotin products in which the biotin has been modified by the addition of alkyl groups, and biotin derivatives such as active esters, amines, hydrazides and thiol groups with the complimentary reactive groups on polymers being amines, acyl and alkyl leaving groups, carbonyl groups and alkyl halides or Michael-type acceptors.

The streptavidin-biotin system represents the strongest non-covalent biological interaction known between a protein and a ligand ($K_a=10^{15}M^{-1}$). Rosebrough, *Nucl. Med. Biol.*, 20: 663–68 (1993). Also, streptavidin has pI of ~6 compared to >10 for avidin, which renders SAv's charge close to neutral at physiological pH in contrast to avidin's strong positive charge. Moreover, avidin is 'sticky' in vivo and in vitro. Rosebrough, supra. For these reasons, streptavidin is preferred to avidin for preparing conjugates used in accordance with the present invention, and the streptavidin/ biotin system is a preferred binding pair for use in the present invention. It is to be understood, however, that either avidin or streptavidin may be used in accordance with the present invention. Accordingly, as used herein, either avidin or streptavidin are intended to include both avidin and streptavidin.

Methods for conjugating biotin and avidin to therapeutic agents and/or antibodies are known, and are described, for example, in co-pending U.S. application Ser. No. 08/486, 166, the contents of which are incorporated herein by reference in their entirety.

When streptavidin (or avidin) is the first member of the binding pair, and biotin is the complementary member of the binding pair, the second conjugate (the biotin-therapeutic agent conjugate) may comprise two or more moieties of biotin. This enhances the conjugates ability to localize at the target site and allows the biotin to cross-link the radiolabeled streptavidin-Mab conjugate pre-targeted at the target sits, inducing internalization of the second therapeutic agent into the targeted tumor cells.

Complementary DNA fragments also may be used as binding pairs. Bos et al., *Cancer Res.* 54: 3479–3486 (1994). Thus, in accordance with the present invention, the first conjugate may comprise antibody, therapeutic agent and a single-stranded oligonucleotide, and the second conjugate may comprise a complementary single-stranded oligonucleotide and a therapeutic agent. A major advantage of this system over biotin/avidin systems could be the presumed lower immunogenicity of a relatively short piece of DNA compared to the immunogenic 60,000 Dalton avidin species.

In another preferred embodiment, the first member of the binding pair is an oligonucleotide analog, such as a single-chain peptide nucleic acid, and the complementary member of the binding pair is the complementary peptide nucleic acid.

Alternatively, the first member of the binding pair may be an enzyme or enzyme substrate, and the complementary member is the corresponding enzyme substrate or enzyme, respectively. Alternatively, a substrate analog may be used in lieu of the enzyme substrate.

Other binding pairs useful in accordance with the present invention are disclosed in the other patents and patent applications discussed herein or will be apparent to those skilled in the art, and the use of such other binding pairs is specifically contemplated.

Therapeutic Agents

The first and second therapeutic agents may be the same or different, and may be, for example, therapeutic radionuclides, drugs, hormones, hormone antagonists, receptor antagonists, enzymes or proenzymes activated by another agent, autocrines or cytokines. Toxins also can be used in the methods of the present invention. Other therapeutic agents useful in the present invention include anti-DNA, anti-RNA, radiolabeled oligonucleotides, such as anti-sense oligodeoxy ribonucleotides, anti-protein and anti-chromatin cytotoxic or antimicrobial agents. Other therapeutic agents are described in the aforementioned U.S. patents and patent applications or are known to those skilled in the art, and the use of such other therapeutic agents in accordance with the present invention is specifically contemplated.

Isotopes, drugs, and toxins are preferred therapeutic agents. While the first and second therapeutic agents may be the same, in a preferred embodiment they are different. For example, the first and second therapeutic agents may comprise different radionuclides, or the first therapeutic agent may comprise a drug while the second therapeutic agent comprises a radionuclide, or the first therapeutic agent may comprise a radionuclide while the second therapeutic agent comprises a drug.

In a preferred embodiment, different isotopes which are effective over different distances as a result of their individual energy emissions are used as first and second therapeutic agents. This achieves more effective treatment of tumors, and is useful in patients presenting with multiple tumors of differing sizes, as in normal clinical circumstances.

As discussed above, few of the available isotopes are useful for treating the very smallest tumor deposits and single cells, and a drug or toxin may be a more useful therapeutic agent in these situations. Accordingly, in preferred embodiments of the present invention, isotopes are used in combination with non-isotopic species such as drugs, toxins, and neutron capture agents.

An isotope can be used in the first step, or in a subsequent step. When the isotope is used in the first step, it is preferred to use readily metabolizable isotopes, such as iodine. Examples of isotopes useful in the first step of the present invention include I-125, I-131 and At-211. When the isotope is used in a subsequent step, it is preferred to use residualizing isotopes, such as yttrium-90. Examples of isotopes useful in the second step of the present invention include P-32, P-33, Sc-47, Cu-64, Cu-67, As-77, Y-90, Rh-105, Pd-109, Ag-111, I-125, Pr-143, Sm-153, Tb-161, Ho-166, Lu-177, Re-186, Re-188, Re-189, Ir-194, Au-199, Pb-212 and Bi-213.

Many drugs and toxins are known which have cytotoxic effects on cells, and can be used in connection with the present invention. They are to be found in compendia of drugs and toxins, such as the Merck Index, Goodman and Gilman, and the like, and in the references cited above.

Examples of known cytotoxic agents useful in the present invention are listed, for example, in Goodman et al., "The Pharmacological Basis of Therapeutics," Sixth Edition, A. G. Gilman et al, eds./Macmillan Publishing Co. New York, 1980. These include taxol, nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used in the methods of the present invention; such drugs are known to these skilled in the art and include puromycin, cycloheximide, and ribonuclease.

Prodrugs are especially useful in the present invention as the inactive precursor of a therapeutic agent because the prodrug is relatively nontoxic in comparison to its active therapeutic metabolite. In the present invention, the prodrug can function as the second conjugate and the complementary member of a binding pair because it is the substrate for an enzyme which is the other member of the binding pair and is a component of the first conjugate. When the first conjugate is administered, it is targeted to the tumor by the targeting moiety. After the first conjugate is allowed sufficient time to localize and a clearing agent is optionally administered, then the prodrug; i.e., the second conjugate is administered. The prodrug binds to the enzyme component of the first conjugate at the tumor and is converted to the active metabolite which kills the tumor. Examples of such enzyme-prodrug binding partners are I-131-antibody-carboxypeptidase G2 and topoisomerase-inhibiting prodrug CPT-11; beta-lactamase and cephalosporin-doxorubicin; alkaline phosphatase and etoposide phosphate; carboxypeptidase G2 and glutamic acid derivative of benzoic acid mustard; and beta-glucuronidase and the glucuronide of any drug which can form a glucuronide, such as p-hydroxyaniline mustard. Other examples of targeted enzymes for prodrug activation are discussed in *Bioconjuate Chem.*, Vol. 4, (1), 3–9 (1993), and in U.S. patent application Ser. No. 07/182,623, which are herein incorporated in their entirety by reference.

The present invention also contemplates dyes used, for example, in photodynamic therapy, and used in conjunction with appropriate non-ionizing radiation. The use of light and porphyrins in methods of the present invention is also contemplated and their use in cancer therapy has been reviewed. van den Bergh, *Chemistry in Britain,* 22: 430–437 (1986), which is incorporated herein in its entirety by reference.

As discussed above, toxins also can be used in the methods of the present invention. Toxins useful as therapeutics are known to those skilled in the art and include plant and bacterial toxins, such as, abrin, alpha toxin, diphtheria toxin, exotoxin, gelonin, pokeweed antiviral protein, ricin, and saporin. Toxins such as RNAases also may be used, for example, onconase may be used.

The other therapeutic agent may be delivered separately from the isotope. For example, a radioiodinated SAv-MAb conjugate may be administered to a patient, as described above. Then, optionally, a clearing agent of an anti-idiotypic MAb may be administered to remove residual circulating radioiodinated conjugate. Next, a biotinylated-polymer-drug conjugate or a biotin-toxin conjugate may be administered in a third step. This particular protocol is preferred for use in the therapy of smaller tumors, micrometastases and even single-cell disease.

It is to be understood that any combination of the above described therapeutic agents may be used. For example, both the first and second therapeutic agents may be radioisotopes, the first therapeutic agent may be a radioisotope and the second therapeutic agent may be a drug, the first therapeutic agent may be a drug and the second therapeutic agent may be a radioisotope, the first therapeutic agent may be a radioisotope and the second therapeutic agent may be a toxin, the first therapeutic agent may be a toxin and the second therapeutic agent may be a radioisotope, both the first and second therapeutic agents may be drugs, or both the first and second therapeutic agents may be toxins.

While the above description teaches the use of two targeting species and two therapeutic agents, the present invention encompasses embodiments where more than two targeting species and/or therapeutic agents are used. For example, mixtures of radiometals which have different optimum ranges in tissue can be used with the same biotin-chelate in a single step. As a particular example, a mixture of the nuclides Y-90 (optimum tissue range 28–42 mm), praseodymium-143 (optimum tissue range 6–11 mm) and lutetium-177 (optimum tissue range 1.2–3.0 mm) can all be radiolabeled by the same biotin-chelate (comprising DTPA or macrocyclic DOTA derivatives, for instance) in the same reaction vessel to give biotin-chelate-complexes with comparable physico-chemical and biological clearance properties that comprise different isotopes. Making these conjugates is facilitated because most radioisotopes useful in radioimmunotherapy are available carrier-free, and many of those are heavy, tricationic metals like Y-90.

When a mixture of therapeutic agents is used, a plurality of therapeutic agents are delivered to the tumor sites, thereby enhancing the benefits of the method. The use of mixtures of nuclides has the further advantage that a greater percentage of the injected biotinylated chelates delivers a nuclidic payload to the tumor target.

Clearing Agents

Clearing agents known in the art may be used in accordance with the present invention. For example, if the first conjugate comprises avidin or streptavidin, biotin may be used as a clearing agent. Alternatively, if the first conjugate comprises biotin, avidin or streptavidin may be used as a clearing agent.

In a preferred embodiment, the clearing agent is an antibody which binds the binding site of the targeting species, where the targeting species can be an antibody, an antigen binding antibody fragment or a non-antibody targeting species. In a more preferred embodiment, the clearing agent is a MAb that is anti-idiotypic to the MAb of the conjugate used in the first step, as described in U.S. application Ser. No. 08/486,166. In another preferred embodiment, the clearing agent is substituted with multiple residues of carbohydrate, such as galactose, which allow the clearing agent to be cleared quickly from circulation by asialoglycoprotein receptors in the liver.

In a more preferred embodiment, the clearing agent is an anti-idiotypic MAb substituted with galactose and small numbers of biotin residues. Different purposes are being accomplished here. The anti-idiotypic MAb clears the first antibody conjugate (radioiodinated MAb-SAv) from circulation and deposits this into the hepatocytes. Because the anti-idiotypic MAb binds to the Mab binding region of the first antibody, it does not remove first antibody conjugate already localized at the tumor sites.

The multiple galactose substitution ensures the rapid clearance of the anti-idiotypic MAb into the liver hepatocytes, usually within minutes. Because the anti-idiotypic MAb is galactosylated and cleared rapidly, it does not have a chance to competitively remove the tumor-localized first antibody conjugate from the tumor over time. Also, there is very little myelotoxicity since almost all circulating radioactivity has been removed from the blood.

The small number of biotin residues on the anti-idiotypic MAb are sufficient to block that fraction of the streptavidin which is cleared into the liver, and remains for an extended period due to its inherent resistance to proteases.

From the above description, it will be evident that the invention can be used advantageously with the pre-targeting and amplification methods described in the above-cited U.S. patents and patent applications. For example, the first antibody conjugate may comprise a polymer to which are attached a plurality of streptavidin moieties, providing an increased number of binding sites for the subsequently administered biotin to bind, as described in U.S. Pat. No. 5,482,698.

The second conjugate of the present invention may comprise a naturally occurring metal-ion chelating protein capable of carrying a plurality of metal ions per protein to amplify the amount of metal ion therapeutic agent delivered to the tumor sites, as described in co-pending U.S. application Ser. No. 08/409,960, the contents of which are incorporated herein by reference in their entirety.

The present invention offers advantages over previous methods which deliver two therapeutic agents to a target site using a pre-targeting step followed by two delivery steps. For example, the method of the present invention has the advantage that each targeting composition has attached thereto a therapeutic agent. This is an advantage because each molecule delivered to the target site delivers a therapeutic agent to the target site, and therapy of the sites is amplified. Also, the present invention achieves delivery of a plurality of therapeutic agents in fewer steps than required by previous methods.

The use of the avidin/biotin binding pair in accordance with the present invention also offers amplification not necessarily achieved by other methods. For example, in the present invention, the avidin of the Ab-avidin-therapeutic agent conjugate has four binding sites available for binding subsequently administered biotin-therapeutic agent conjugates. In contrast, in other pre-targeting methods, one of the biotin-binding sites is used to target the avidin to the target site, for example, by binding to a biotin pre-targeted at the target site. This leaves only three biotin-binding sites available for binding the subsequently administered biotin conjugate. Thus, the present invention allows more biotin-therapeutic agent conjugate to be localized at the tumor sites.

EXAMPLES

The embodiments of the invention may be further illustrated through examples which show aspects of the invention in detail. These examples illustrate specific elements of the invention and are not to be construed as limiting the scope thereof.

Example 1

Targeted Double Therapeutic Agents

Preferred embodiments of targeted double therapeutic agents that can be delivered utilizing the method of the present invention include but are not limited to the following systems:

(1) I-131-antibody-biotin cleared (and tumor-avidinylated) with neutralized, deglycosylated avidin and targeted secondarily with Y-90-chelate-biotin.

(2) I-131-antibody-biotin cleared with an anti-idiotypic antibody, tumor-avidinylated with neutralized, deglycosylated avidin and targeted secondarily with Y-90-chelate-biotin.

(3) I-131-antibody-streptavidin cleared with an anti-idiotypic antibody and targeted secondarily with Y-90-chelate-biotin.

(4) I-131-antibody-streptavidin cleared with an anti-idiotypic antibody and targeted secondarily with Lu-177-chelate-biotin.

(5) I-131-antibody-streptavidin cleared with an anti-idiotypic antibody and targeted secondarily with camptothecin-biotin.

(6) I-131-antibody-streptavidin cleared with an anti-idiotypic antibody and targeted secondarily with onconase-biotin.

(7) I-131-antibody-streptavidin cleared with an anti-idiotypic antibody and targeted secondarily with pokeweed antiviral protein-biotin.

(8) I-131-antibody-streptavidin cleared with an anti-idiotypic antibody and targeted secondarily with endostatin-biotin.

(9) I-131-antibody-avidin (optionally neutralized and deglycosylated) cleared with an anti-idiotypic antibody and targeted secondarily with gelonin-biotin.

(10) I-131-bispecific antibody (such as anti-CEA and anti-Y-DOTA chelate) cleared with an anti-idiotypic antibody and targeted secondarily by a Y-90-DOTA derivative.

(11) I-131-bispecific antibody (such as anti-CEA and anti-doxorubicin) cleared with an anti-idiotypic antibody and targeted secondarily by a doxorubicin analog.

(12) I-131-bispecific antibody (such as anti-CEA and anti-ricin A chain) cleared with an anti-idiotypic antibody and targeted secondarily by a ricin A analog.

(13) I-131-biotinylated bispecific antibody (such as anti-CEA and anti-Y-DOTA chelate) cleared (and streptavidinylated at the tumor) with streptavidin and targeted secondarily by a Y-90-DOTA-biotin.

(14) I-131-antibody-avidin (optionally neutralized and deglycosylated) cleared with an anti-idiotypic antibody and targeted secondarily with I-125-antibody(3)-biotin.

(15) I-131-antibody-avidin (optionally neutralized and deglycosylated) cleared with an anti-idiotypic antibody and targeted secondarily with $(Y-90-DOTA)_8$-dextran-biotin.

(16) I-131-antibody-carboxypeptidase G2 cleared with an anti-idiotypic antibody and targeted secondarily with the topoisomerase-inhibiting prodrug CPT-11.

(17) I-131-antibody-avidin (optionally neutralized and deglycosylated) cleared with an anti-idiotypic antibody and targeted secondarily with ($^{10}$B-carborane)$_8$-dextran-biotin. The boron addend, targeted B-10, is then irradiated with thermal or epithermal neutrons to initiate neutron capture and generate cytotoxic alpha-particle and recoil nuclei. Examples of boron addends are described in copending U.S. patent application Ser. No. 08/687,626, which is herein incorporated by reference in its entirety.

In all of the above recited embodiments, there are little or no other non-target tissue binding sites available due to the clearance and metabolism of the first conjugate. In a preferred embodiment, the secondary recognition system utilized is foreign to the body being treated, thus minimizing non-specific binding and resulting in the attainment of a truer form of tumor specific targeting.

The therapeutic agents can be polymeric. In embodiment (11) above, doxorubicin analogs include the free drug, doxorubicin-dextran polymers and doxorubicin-PEG derivatives. PEG derivatives of second therapeutic agents are especially noteworthy because the serum residence time of such agents can be carefully controlled so that agents circulate for a sufficient period of time to saturate all pre-targeted tumor sites.

Embodiment 13 includes two recognition systems on the second conjugate; i.e., an antibody based and a biotin-steptavidin based recognition of the Y-90 therapy agent.

In embodiment (8), endostatin is an angiogenesis-inhibiting agent, similar to angiostatin.

Embodiments (5) and (11) are examples of employing commonly available anti-cancer drugs in the claimed methods, which is an advantage because these drugs can be administered in reduced amounts, and thus are less toxic, as compared to administering the free drug alone. Further, the receptor site for the drug is only present at the tumor, thus enhancing the tumor-to-tissue localization ratio. Generally, any standard chemotherapy drug can be used within the scope of the present invention but it is preferred that the major limiting toxicities of the two therapeutic agents be different. For example, myelosuppresssion is the major limiting toxicity of radioimmunotherapy, and it is not further increased by the use of bleomycin as the second therapy agent because its major limiting toxicity is pulmonary fibrosis.

Embodiment 14 as described in U.S. Pat. No. 5,525,338, herein incorporated in its entirety by reference, discloses the use of secondary targeted antibodies within pretargeting protocols. In this embodiment, the use of biotin-avidin recognition is supplemented by antibody (3) recognition of the same or a different epitope on the original target cell. In a similar manner, embodiment 15 as described in U.S. Pat. No. 5,482,698, herein incorporated in its entirety by reference, discloses many polymeric materials which enable amplification of targeting.

Embodiment 16 discloses a preferred embodiment which utilizes a prodrug within the scope of the present invention. Specifically, this embodiment uses the prodrug's relative lack of toxicity in comparison to its more active metabolite (i.e., SN-38), to further increase the difference between tumor and normal tissue toxicological effects.

Example 2

Targeting of a CEA-Producing Tumor with Two Different Radionuclides

Nude mice bearing approximately one week old GW-39 (CEA-producing) human tumor xenografts are treated with an injection of a Y-88-DTPA-MN14 (anti-CEA)-streptavidin radioimmunoconjugate. Forty-eight hours later the animals are treated with a five-fold molar excess (to remaining MN-14 in the circulation) of an anti-idiotypic antibody to MN14; WI2. Three hours later animals are injected with biotin-D-Phe- (epsilon-In-lll-Bz-DTPA)-D-LysNH$_2$. After sacrifice and necropsy important tissues are counted separately in a gamma-scintillation counter using energy window settings appropriate for the two radionuclides; which, decaying at very different energies, can therefore be counted simultaneously. FIG. 1 shows the percentage ID/g of both agents in tumor at continuing time-points, while FIG. 2 shows the tumor-to-blood ratios for the reagents. It is found that tumor-to-blood ratios for the subsequently-administered biotin-D-Phe-(epsilon-In-lll-Bz-DTPA)-D-LysNH$_2$ reach well over 100:1 within a very short time. Tumor-to-blood ratios of the Y-88-DTPA-MN14 also are around 80–100:1 at the time-points test. In comparison, Y-88-streptavidin-MN14 alone (as a model for standard radioimmunotherapy) only has a 2:1 tumor-to-blood ratio as late as 72 hours post-injection.

Example 3

Three-Step Radioimmunotherapy Delivering I-125 or I-131 and Y-90 to Tumor Sites In this example a first antibody conjugate which comprises an anti-tumor MAb conjugated to streptavidin (SAv) and radiolabeled with an iodine isotope, such as I-131 or I-125, is administered to a patient.

After time of maximum tumor accretion, for example, about 24 to about 48 hours, a clearing composition comprising a conjugate of a MAb that is anti-idiotypic to the antibody of the first antibody conjugate is administered. This clearing agent clears first antibody conjugate from circulation.

The radioiodinated MAb-SAv localized at the tumor sites remains there, irradiating the tumor over very short ranges in the case of I-125 (single cell diameters) or over short to medium ranges in the case of I-131 (optimum range 0.26 to 0.5 cm). The radioiodinated MAb-SAv deposited internally in liver hepatocytes is metabolized and, the radioiodine is released and rapidly excreted from the patient.

Then, a conjugate is administered which comprises a biotinylated chelate carrying a radiometallic therapeutic nuclide, such as Y-90, as the second therapeutic agent. Because of the great affinity of biotin for streptavidin, the biotin-chelate-Y-90 conjugate rapidly binds to the tumor via the SAv moieties localized at the tumor site during the previous steps. Because the biotin-chelate-Y-90 conjugate is a low molecular weight species, non-localized conjugate is rapidly eliminated from the patient via the urine. Thus, a second therapeutic dose of radionuclide is delivered to the tumor site with minimal myelotoxicity.

Example 4

Three-Step Radioimmunotherapy Delivering I-131 and P-32 to Tumor Sites

This example takes advantage of the therapeutic effects of longer-lived nuclides and of the fact that nuclides localized at tumor sites in accordance with the present invention stay at the site for an extended period of time. This example also illustrates the use of a pair of complimentary oligonucleotides as binding partners.

In the first step, a radioiodinated conjugate of a targeting MAb and a single-strand of an oligonucleotide, such as polyguanine, is administered. A galactosylated anti-idiotypic MAb is given at the time of maximum tumor localization to clear circulating first MAb conjugate, as discussed above. The second therapeutic isotope, P-32, is administered in the form of enzyme-resistant phosphorothioate esters bound to the single strand of an oligonucleotide that is complimentary to the one used in the first step, in this case, polycytosine.

By this method, both I-131 and P-32 are delivered to the tumor sites.

Example 5

Therapy Delivering a Drug and Radioisotope to Tumor Sites

An SAv-MAb conjugate substituted with multiple drug moieties is administered to a patient. While a clearing agent step may be performed, it is optional. Because the initial conjugate is not carrying a radioactive isotope, omitting the clearing agent step should not have an adverse affect on the patient.

At the time of maximum tumor accretion a multi-biotinylated-polymer-lutetium-177 conjugate is given. That is, the conjugate comprises two or more biotin moieties. This latter conjugate binds to the SAv-MAb conjugate already localized at the tumor sites, cross-links the SAv-MAb conjugate and induces apoptosis and internalization. The tumor is then irradiated with the internalized, retained lutetium-177 radionuclide over an extended period, due to the nuclide's 7 day half-life.

In another variation of this example, a mixture or "cocktail" of isotopes is used in the second step. Preferably, isotopes with different effective ranges are used.

Example 6

Combined Radioimmunotherapy and Toxin Immunotherapy Using a Three-Step Protocol An iodine-131-labeled streptavidin-mAb conjugate is administered to a patient by injection. At the time of maximum tumor accretion of the conjugate, a circulatory clearing dose of a lightly biotinylated anti-idiotypic antibody is administered. This clearing agent removes non-targeted conjugate from the blood, and the I-131 is rapidly catabolized from the protein in the liver and is excreted. Conjugate targeted to the tumor sites remains at the tumor sites for an extended period of time, and irradiates the tumor cells. In the third step, the patient is injected with a toxin conjugate of $(biotin)_2$-onconase. The toxin localizes to the tumor sites via the pre-targeted streptavidin moieties. The doubly-biotinylated onconase is able to bind and cross-link the streptavidin-Mab conjugate, inducing internalization of the toxin into the tumor cells, which have already been irradiated with I-131, thereby effecting dual therapy of the tumor cells.

Example 7

Combined Radioimmunotherapy and Drug Immunotherapy Using a Three-Step Protocol An iodine-131-labeled streptavidin-MAb conjugate is administered to a patient by injection. At the time of maximum tumor accretion of the conjugate, a circulatory clearing dose of a lightly biotinylated anti-idiotypic antibody is administered. This clearing agent removes non-targeted conjugate from the blood, and the 1-131 is rapidly catabolized from the protein in the liver and is excreted. Conjugate targeted to the tumor sites remains at the tumor sites for an extended period of time, and irradiates the tumor cells.

In the third step, the patient is injected with a drug conjugate of $(biotin)_2$-dextran-$(doxorubicin)_{10}$. The drug localizes to the tumor sites via the pre-targeted streptavidin moieties. The doubly-biotinylated polymeric drug is able to bind and cross-link the streptavidin-Mab conjugate, inducing internalization of the doxorubicin into the tumor cells, which have already been irradiated with I-131, thereby effecting dual therapy of the tumor cells.

It will be apparent to those skilled in the art that various modifications and variations can be made to the processes and compositions of this invention. Thus, it is intended that the present invention cover the modifications and variations of this invention provided they come within the scope of the appended claims and their equivalents.

We claim:

1. A composition for effecting therapy of a tumor in a patient, comprising:
    (A) a first conjugate comprising a targeting moiety, a first member of a binding pair, and a first therapeutic agent, wherein the targeting moiety selectively binds to a marker substance produced by or associated with the tumor;
    (B) optionally, a clearing agent; and
    (C) a second conjugate comprising a complementary member of said binding pair and a second therapeutic agent, wherein the second therapeutic agent is the same as or different from the first therapeutic agent,
    wherein the binding pair is selected from the group consisting of (a) complementary DNA fragments, (b) complementary peptide oligonucleotides, and (c) corresponding enzymes and prodrug substrates.

2. The composition of claim 1, wherein the first and second therapeutic agents are selected from the group consisting of radionuclides, drugs, toxins, and boron addends.

3. The composition of claim 2, wherein the first and second therapeutic agents are radionuclides.

4. The composition of claim 3, wherein each of the radionuclides emit different levels of radiation.

5. The composition of claim 3, wherein the first therapeutic agent is selected from the group consisting of I-131, I-125 and At-211.

6. The composition of claim 3, wherein the second therapeutic agent is selected from the group consisting of P-32, P-33, Sc-47, Cu-64, Cu-67, As-77, Y-90, Ph-105, Pd-109, Ag-111, I-125, Pr-143, Sm-153, Tb-161, Ho-166, Lu-177, Re-186, Re-188, Re-189, Ir-194, Au-199, Pb-212, and Bi-213.

7. The composition of claim 2, wherein the second therapeutic agent is a boron addend.

8. The composition of claim 2, wherein the first and second therapeutic agents are mixtures of at least two radionuclides, drugs, toxins or boron addends.

9. The composition of claim 2, wherein the first therapeutic agent is a radionuclide and the second therapeutic agent is a drug, a toxin, or a boron addend.

10. The composition of claim 9, wherein the first therapeutic agent is selected from the group consisting of I-131, I-125 and At-211.

11. The composition of claim 9, wherein the second therapeutic agent is a drug selected from the group consisting of taxol, nitrogen mustards, ethylenimine derivatives, alkyl sulfonates, nitrosoureas, triazenes, folic acid analogs, pyrimidine analogs, purine analogs, vinca alkaloids, antibiotics, enzymes, platinum coordination complexes, substituted urea, methyl hydrazine derivatives, adrenocortical suppressants, hormones, antagonists, camptothecin, and endostatin.

12. The composition of claim 9, wherein the second therapeutic agent is a toxin selected from the group consisting of abrin, alpha toxin, diphtheria toxin, exotoxin, gelonin, pokeweed antiviral protein, ricin, saporin, and onconase.

13. The composition of claim 2, wherein the first therapeutic agent is a drug or toxin and the second therapeutic agent is a radionuclide or a boron addend.

14. The composition of claim 13, wherein the first therapeutic agent is a drug selected from the group consisting of taxol, nitrogen mustards, ethylenimine derivatives, alkyl sulfonates, nitrosoureas, triazenes, folic acid analogs, pyrimidine analogs, purine analogs, vinca alkaloids, antibiotics, enzymes, platinum coordinations complexes, substituted urea, methyl hydrazine derivatives, adrenocortical suppressants, hormones, antagonists, camptothecin, and endostatin.

15. The composition of claim 13, wherein the first therapeutic agent is a toxin selected from the group consisting of abrin, alpha toxin, diphtheria toxin, exotoxin, gelonin, pokeweed antiviral protein, ricin, saporin, and onconase.

16. The composition of claim 14, wherein the second therapeutic agent is a radionuclide selected from the group consisting of P-32, P-33, Sc-47, Cu-64, Cu-67, As-77, Y-90, Ph-105, Pd-109, Ag-111, I-125, I-131, Pr-143, Sm-153, Tb-161, Ho-166, Lu-177, Re-186, Re-188, Re-189, Ir-194, Au-199, At-211, Pb-212, and Bi-213.

17. The composition of claim 14, wherein the second therapeutic agent is a boron addend.

18. The composition of claim 15, wherein the second therapeutic agent is a radionuclide selected from the group consisting of P-32, P-33, Sc-47, Cu-64, Cu-67, As-77, Y-90, Ph-105, Pd-109, Ag-111, I-125, I-131, Pr-143, Sm-153, Tb-161, Ho-166, Lu-177, Re-186, Re-188, Re-189, Ir-194, Au-199, At-211, Pb-212, and Bi-213.

19. The composition of claim 15, wherein the second therapeutic agent is a boron addend.

20. The composition of claim 1, wherein the targeting moiety is an antibody or an antigen-binding antibody fragment.

21. The composition of claim 20, wherein the antibody is a bispecific antibody capable of specifically binding to at least one epitope on the marker substance or on a component of the second conjugate.

22. The composition of claim 1, wherein the targeting moiety is selected from the group consisting of proteins, peptides, polypeptides, enzymes, and oligonucleotides.

23. The composition of claim 1, wherein the binding pair is selected from the group consisting of complementary DNA fragments and complementary peptide oligonucleotides.

24. A composition for effecting therapy of a tumor in a patient, comprising:
   (A) a first conjugate comprising a targeting moiety, a first member of a binding pair, and a first therapeutic agent, wherein the targeting moiety selectively binds to a marker substance produced by or associated with a tumor;
   (B) optionally, a clearing agent; and
   (C) a second conjugate comprising a complementary member of said binding pair and a second therapeutic agent, wherein the second therapeutic agent is the same as or different from the first therapeutic agent, wherein the clearing agent is anti-idiotypic to the targeting moiety of the first conjugate.

25. The composition of claim 24, wherein the clearing agent is an anti-idiotypic monoclonal antibody.

26. The composition of claim 25, wherein the anti-idiotypic monoclonal antibody is substituted with galactose and biotin residues.

27. The composition of claim 1, wherein the first and second conjugates contain radionuclides which emit different levels of radiation.

28. The composition of claim 27, wherein the clearing agent is an anti-idiotypic monoclonal antibody substituted with galactose and biotin residues.

29. The composition of claim 1, wherein the first member of the binding pair of the first conjugate comprises an enzyme and the second conjugate comprises a prodrug which is converted to a drug by the enzyme, wherein the prodrug comprises both the complementary member of the binding pair and the second therapeutic agent.

30. The composition of claim 29 wherein said second therapeutic agent is the same as or different from said first therapeutic agent, wherein said enzyme is carboxypeptidase G2 and said prodrug is CPT-11.

31. The composition of claim 29, wherein the first therapeutic agent is a radionuclide.

32. A kit for effecting therapy of a tumor in a patient, comprising, in separate containers:
   (A) a first conjugate comprising a targeting moiety, a first member of a binding pair, and a first therapeutic agent, wherein the targeting moiety selectively binds to a marker substance produced by or associated with a tumor;
   (B) optionally, a clearing agent; and
   (C) a second conjugate comprising a complementary member of the binding pair and a second therapeutic agent, wherein the second therapeutic agent is the same as or different from the first therapeutic agent.

33. A method for effecting therapy of a tumor in a patient comprising:
   (A) administering to the patient a first conjugate comprising a targeting moiety, a first member of a binding pair, and a first therapeutic agent, wherein the targeting moiety selectively binds to a marker substance produced by or associated with a tumor, and allowing the first conjugate to localize at the tumor, thereby effecting therapy of the tumor;
   (B) optionally, administering to the patient a clearing agent, and allowing the clearing agent to clear non-localized first conjugate from circulation; and
   (C) administering to the patient a second conjugate comprising a complementary member of the binding pair and a second therapeutic agent, wherein the second therapeutic agent is the same as or different from the first therapeutic agent, and allowing the second conjugate to localize at the tumor, thereby effecting therapy of the tumor.

34. The kit of claim 32, wherein the second therapeutic agent is a boron addend.

35. The method of claim 34, which further comprises irradiating the tumor with thermal or epithermal neutrons after the localization of the second conjugate at the tumor.

36. A composition for effecting therapy of a tumor in a patient, comprising:
   (A) a first conjugate comprising a multispecific targeting moiety which binds to at least one epitope on a marker substance produced by or associated with the tumor cells and with at least one epitope of a component of the second conjugate, a first member of a binding pair, and a first therapeutic agent;
   (B) optionally, a clearing agent; and
   (C) a second conjugate comprising a complementary member of said binding pair and a second therapeutic agent, wherein the second therapeutic agent is the same as or different from the first therapeutic agent.

37. A composition as claimed in claim 36, wherein said multispecific targeting moiety is a bispecific or hybrid antibody.

* * * * *